US00PP12978P2

(12) United States Plant Patent
den Haan

(10) Patent No.: US PP12,978 P2
(45) Date of Patent: Sep. 17, 2002

(54) LEUCANTHEMUM PLANT NAMED 'KIEMAR'

(75) Inventor: Pieter den Haan, Steenbergen (NL)

(73) Assignee: Kieft Seeds Holland, Venhuizen (NL)

( * ) Notice: Subject to any disclaimer, the term of this patent is extended or adjusted under 35 U.S.C. 154(b) by 39 days.

(21) Appl. No.: 09/834,563

(22) Filed: Apr. 13, 2001

(51) Int. Cl.[7] ..... A01H 5/00

(52) U.S. Cl. ..... Plt./285

(58) Field of Search ..... Plt./285, 284

*Primary Examiner*—Bruce R. Campell
*Assistant Examiner*—June Hwu
(74) *Attorney, Agent, or Firm*—C. A. Whealy

(57) ABSTRACT

A distinct cultivar of Leucanthemum plant named 'Kiemar', characterized by its upright, compact and uniform plant habit; dark green foliage; early flowering habit; daisy-type inflorescences; white-colored ray florets and bright yellow-colored disc florets; and good garden performance.

1 Drawing Sheet

BACKGROUND OF THE INVENTION

The present Invention relates to a new and distinct cultivar of Leucanthemum plant, botanically known as *Chrysanthemum leucanthemum* and hereinafter referred to by the name 'Kiemar'.

The new Leucanthemum is a product of a planned breeding program conducted by the Inventor in Steenbergen, The Netherlands. The objective of the breeding program is to create compact Leucanthemum cultivars that flower early and have good garden performance.

The new Leucanthemum originated from a cross made by the Inventor in the summer of 1993, in Steenbergen, The Netherlands, of two unidentified seedling selections of *Chrysanthemum leucanthemum*. The new Leucanthemum was discovered and selected by the Inventor as a single flowering plant within the progeny of the stated cross grown in a controlled environment in Steenbergen, The Netherlands in the summer of 1995. The selection of this plant was based on its compact plant habit and early flowering.

Asexual reproduction of the new Leucanthemum by vegetative tip cuttings was first conducted in Steenbergen, The Netherlands in 1997. Asexual reproduction by cuttings has shown that the unique features of this new Leucanthemum are stable and reproduced true to type in successive generations.

SUMMARY OF THE INVENTION

The cultivar Kiemar has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Kiemar'. These characteristics in combination distinguish 'Kiemar' as a new and distinct Leucanthemum:

1. Upright, compact and uniform plant habit.
2. Dark green foliage.
3. Early flowering.
4. Daisy-type inflorescences that are about 5 cm in diameter.

5. White-colored ray florets and bright yellow-colored disc florets.
6. Good garden performance.

Plants of the new Leucanthemum have been observed to be more compact and stronger than plants of the parent selections.

Plants of the new Leucanthemum can be compared to plants of the seed-propagated Leucanthemum cultivar White Knight not patented. In side-by-side comparisons conducted by the Inventor in Steenbergen, The Netherlands, plants of the new Leucanthemum differ from plants of the cultivar White Knight in the following characteristics:

1. Plants of the new Leucanthemum flower about three weeks earlier than plants of the cultivar White Knight.
2. Plants of the new Leucanthemum are stronger than plants of the cultivar White Knight.

BRIEF DESCRIPTION OF THE PHOTOGRAPHS

The accompanying colored photographs illustrate the overall appearance of the new Leucanthemum showing the colors as true as it is reasonably possible to obtain in colored reproductions of this type. Colors in the photographs may differ from the color values cited in the detailed botanical description which accurately describe the colors of the new Leucanthemum.

The photograph at the top of the sheet comprises a side perspective view of a typical flowering plant of 'Kiemar'.

The photograph at the bottom of the sheet comprises a close-up view of typical developing inflorescences and leaves of 'Kiemar'. Plants used in the photographs were about 10 weeks from planting unrooted cuttings.

DETAILED BOTANICAL DESCRIPTION

The cultivar Kiemar has not been observed under all possible environmental conditions. The phenotype may vary somewhat with variations in environment such as temperature, light intensity, water status, and fertilizer rates without, however, any variance in genotype. The following observations, measurements and comparisons describe plants grown in Lompoc, Calif., under commercial practice during the winter in a polycarbonate-covered greenhouse with day temperatures about 18 to 24° C., night temperatures about 16 to 18° C. and light levels about 4,000 to 8,000 foot-candles. Unrooted cuttings were directly planted in 15-cm containers and grown for about 10 weeks.

In the following description, color references are made to The Royal Horticultural Society Colour Chart except where general terms of ordinary dictionary significance are used.

Botanical classification: *Chrysanthemum leucanthemum* cultivar Kiemar.

Parentage:

*Female, or seed, parent*.—Unidentified seedling selection of *Chrysanthemum leucanthemum,* not patented.

*Male, or pollen, parent*.—Unidentified seedling selection of *Chrysanthemum leucanthemum,* not patented.

Propagation:

*Type*.—Terminal tip cuttings.

*Time to initiate roots*.—Summer: About 14 days. Winter: About 18 days.

*Time to produce a rooted cutting*.—Summer: About 21 to 24 days. Winter: About 26 to 28 days.

*Root description*.—Fibrous, white.

*Rooting habit*.—Freely branching.

Plant description:

*Appearance*.—Compact, upright and uniform plant habit. Freely basal branching with about 16 lateral branches per plant. Moderate vigor.

*Plant height*.—About 19 cm.

*Plant width*.—About 20 cm.

*Lateral branches*.—Length: About 17 cm. Diameter: About 3 mm. Internode length: About 1.8 cm. Strength: Strong. Texture: Glabrous, longitudinally ridged. Color: 146A.

*Foliage description*.—Arrangement: Alternate, simple. Quantity of leaves per lateral stem: About 12. Length: About 4.7 cm. Width: About 1.3 cm. Shape: Oblong to lyrate. Apex: Rounded to broadly acute. Base: Attenuate. Margin: Laciniate. Texture: Smooth, glabrous. Venation pattern: Pinnate. Color: Young foliage, upper surface: 137A. Young foliage, lower surface: 137B. Mature foliage, upper surface: 147A. Mature foliage, lower surface: 137B. Venation, upper surface: 147C. Venation, lower surface: 137C. Petiole: Length: About 4 mm. Diameter: About 6 mm. Color: 147C.

Inflorescence description:

*Appearance*.—Daisy-type inflorescence form with elongated oblong-shaped ray florets. Inflorescences borne on terminals above foliage. Disk and ray florets arranged acropetally on a capitulum. Inflorescences persistent. Not fragrant. Typically one terminal inflorescence per lateral branch.

*Flowering response*.—Under natural conditions, plants flower in the spring. Under greenhouse conditions, plant flower year-round. Early flowering, plants begin to flower about four weeks after planting cuttings.

*Inflorescence longevity*.—Inflorescences maintain good color and substance for about 7 days on the plant.

*Inflorescence bud*.—Height: About 7 mm. Diameter: About 1 cm. Shape: Flattened sphere. Color: 145D.

*Inflorescence size*.—Diameter: About 5 cm. Depth (height): About 1 cm. Diameter of disc: About 1.5 cm. Receptacle diameter: About 7 mm. Receptacle height: About 3 mm.

*Ray florets*.—Shape: Elongated-oblong, ligulate with longitudinal ridges. Orientation: Initially upright, then about 90° from vertical or perpendicular to peduncle. Aspect: Initially incurved, then reflexed. Length: About 2.3 cm. Width: About 8 mm. Apex: Emarginate. Base: Acute; short corolla tube. Margin: Entire. Texture: Smooth, glabrous, velvety. Number of ray florets per inflorescence: About 23 arranged in two rows. Color: When opening, upper and lower surfaces: 155A. Fully opened, upper and lower surfaces: More white than 155D.

*Disc florets*.—Arrangement: Massed at center of receptacle. Shape: Tubular, elongated. Apex: Five-pointed. Length: About 6 mm. Width: About 1.5 mm. Number of disc florets per inflorescence: About 320. Color, immature and mature: Apex: 7A. Mid-section and base: 144D.

*Phyllaries*.—Quantity/arrangement: About 40 to 45 in imbricate whorls. Shape: Elliptic. Apex: Acute. Margin: Entire, membranous. Texture: Smooth, glabrous. Length: About 4.5 mm. Width: Less than 1 mm. Color: Upper surface: 144D. Lower surface: 144B.

*Reproductive organs*.—Androecium: Present on disc florets only. Stamen quantity: Five. Anther shape: Oval. Anther length: Less than 1 mm. Anther color: 7A. Pollen amount: Scarce. Pollen color: 7A. Gynoecium: Present on both ray and disc florets. Pistil quantity: One. Pistil length: About 5 mm. Stigma shape: Bi-lobed. Stigma color: 10A. Style length: About 4 mm. Style color: 145C. Ovary color: 145D.

*Seed*.—Seed production has not been observed.

Disease/pest resistance: Resistance to pathogens and pests common to Leucanthemums has not been observed on plants grown under commercial greenhouse conditions.

Garden performance: Plants of the new Leucanthemum have been observed to be tolerant to rain and wind.

It is claimed:

1. A new and distinct cultivar of Leucanthemum plant named 'Kiemar', as illustrated and described.

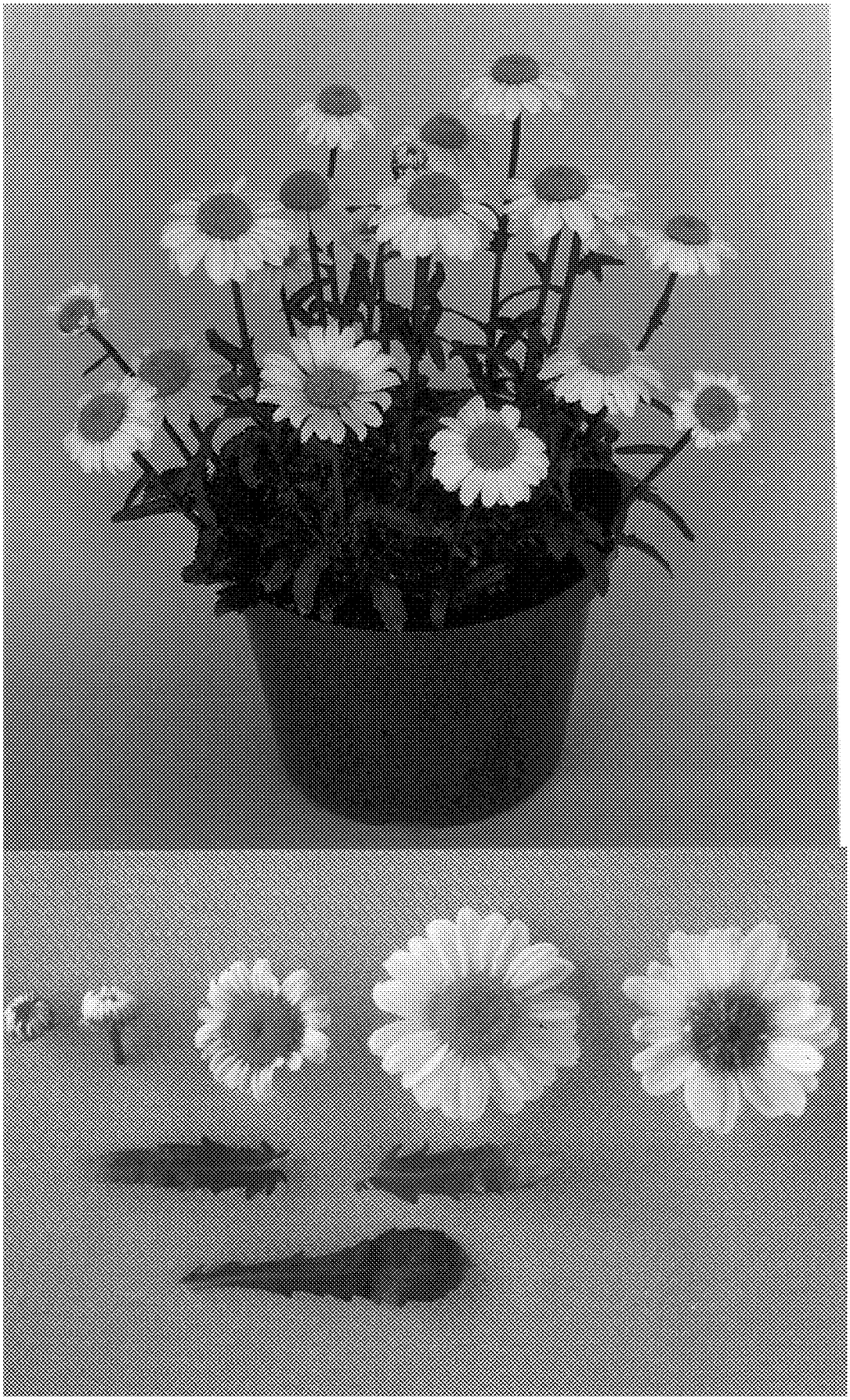

* * * * *